US00PP19692P2

(12) United States Plant Patent
Heinrich

(10) Patent No.: US PP19,692 P2
(45) Date of Patent: Feb. 10, 2009

(54) ***SANVITALIA* PLANT NAMED 'WESSATEQ'**

(50) Latin Name: *Sanvitalia procumbens*
Varietal Denomination: WESSATEO

(75) Inventor: Westhoff Heinrich, Südlohn (DE)

(73) Assignee: Gartenbau und Spezialkulturen Westhoff Gbr, Südlohn (DE)

( * ) Notice: Subject to any disclaimer, the term of this patent is extended or adjusted under 35 U.S.C. 154(b) by 0 days.

(21) Appl. No.: 11/983,741

(22) Filed: Nov. 12, 2007

(51) Int. Cl.
*A01H 5/00* (2006.01)

(52) U.S. Cl. ..... Plt./476

(58) Field of Classification Search ..... Plt./476
See application file for complete search history.

*Primary Examiner*—Annette H Para
*Assistant Examiner*—June Hwu
(74) *Attorney, Agent, or Firm*—C. A. Whealy

(57) ABSTRACT

A new and distinct cultivar of *Sanvitalia* plant named 'Wessateq', characterized by its compact, outwardly spreading and mounding plant habit; freely branching growth habit; freely flowering habit; dark green-colored leaves; bright yellow-colored inflorescences; and good garden performance.

1 Drawing Sheet

Botanical designation: *Sanvitalia procumbens.*
Cultivar denomination: 'WESSATEQ'.

BACKGROUND OF THE INVENTION

The present invention relates to a new and distinct cultivar of *Sanvitalia,* botanically known as *Sanvitalia procumbens* and hereinafter referred to by the name 'Wessateq'.

The new *Sanvitalia* is a product of a planned breeding program conducted by the Inventor in Südlohn, Germany. The objective of the breeding program was to create new compact and mounded *Sanvitalia* cultivars with numerous attractive flowers.

The new *Sanvitalia* originated from a cross-pollination made by the Inventor in 2004, in Südlohn, Germany, of a proprietary selection of *Sanvitalia procumbens* identified as code number 04P006, not patented, as the female, or seed, parent with a proprietary selection of *Sanvitalia procumbens* identified as code number 04P003, not patented, as the male, or pollen, parent. The new *Sanvitalia* was discovered and selected by the Inventor as a single flowering plant within the progeny of the stated cross-pollination in a controlled environment in Südlohn, Germany in 2005.

Asexual reproduction of the new *Sanvitalia* by vegetative cuttings in a controlled environment in Südlohn, Germany since 2005 has shown that the unique features of this new *Sanvitalia* are stable and reproduced true to type in successive generations.

SUMMARY OF THE INVENTION

The cultivar Wessateq has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Wessateq'. These characteristics in combination distinguish 'Wessateq' as a new and distinct cultivar of *Sanvitalia:*

1. Compact, outwardly spreading and mounding plant habit.
2. Freely branching growth habit.
3. Freely flowering habit.
4. Dark green-colored leaves.
5. Bright yellow-colored inflorescences.
6. Good garden performance.

Plants of the new *Sanvitalia* differ from plants of the female parent selection in the following characteristics:

1. Plants of the new *Sanvitalia* have stronger lateral branches than plants of the female parent selection.
2. Plants of the new *Sanvitalia* have smaller leaves than plants of the female parent selection.
3. Plants of the new *Sanvitalia* have smaller inflorescences than plants of the female parent selection.

Plants of the new *Sanvitalia* differ from plants of the male parent selection in the following characteristics:

1. Plants of the new *Sanvitalia* are more compact than plants of the male parent selection.
2. Plants of the new *Sanvitalia* are more freely flowering than plants of the male parent selection.

Plants of the new *Sanvitalia* can be compared to plants of the *Sanvitalia* cultivar Wessacomp, disclosed in U.S. Plant Pat. No. 15,881. In side-by-side comparisons conducted in S üdlohn, Germany, plants of the new *Sanvitalia* differed from plants of the cultivar Wessacomp in the following characteristics:

1. Plants of the new *Sanvitalia* were larger and more vigorous than plants of the cultivar Wessacomp.
2. Plants of the new *Sanvitalia* had longer internodes than plants of the cultivar Wessacomp
3. Plants of the new *Sanvitalia* had larger leaves than plants of the cultivar Wessacomp.

Plants of the new *Sanvitalia* can also be compared to plants of the *Sanvitalia* cultivar Wessastar, disclosed in U.S.

Plant Pat. No. 14,799. In side-by-side comparisons conducted in Südlohn, Germany, plants of the new *Sanvitalia* differed from plants of the cultivar Wessastar in the following characteristics:

1. Plants of the new *Sanvitalia* were more compact and had shorter internodes than plants of the cultivar Wessastar.
2. Plants of the new *Sanvitalia* had smaller leaves than plants of the cultivar Wessastar.

BRIEF DESCRIPTION OF THE PHOTOGRAPH

The accompanying colored photograph illustrates the overall appearance of the new *Sanvitalia,* showing the colors as true as it is reasonably possible to obtain in colored reproductions of this type. Colors in the photograph may differ slightly from the color values cited in the detailed botanical description which accurately describe the colors of the new *Sanvitalia.* The photograph comprises a side perspective view of a typical flowering plant of 'Wessateq' grown in a container.

DETAILED BOTANICAL DESCRIPTION

The aforementioned photograph and following observations, measurements and values describe plants grown in Südlohn, Germany, under commercial practice during the summer in a glass-covered greenhouse with day temperatures ranging from 20° C. to 25° C., night temperatures ranging from 16° C. to 18° C. and light levels ranging from 3,000 lux to 50,000 lux. Rooted young plants were grown for about 20 weeks when the photograph and description were taken. In the following description, color references are made to The Royal Horticultural Society Colour Chart, 2001 Edition, except where general terms of ordinary dictionary significance are used.

Botanical classification: *Sanvitalia procumbens* cultivar Wessateq.

Parentage:

*Female, or seed parent.*—Proprietary selection of *Sanvitalia procumbens* identified as code number 04P006, not patented.

*Male, or pollen, parent.*—Proprietary selection of *Sanvitalia procumbens* identified as code number 04P003, not patented.

Propagation:

*Type.*—By vegetative cuttings.

*Time to initiate roots, summer.*—About 10 to 14 days at temperatures of 20° C.

*Time to initiate roots, winter.*—About 16 to 18 days at temperatures of 20° C.

*Time to produce a rooted young plant, summer.*—About 21 to 24 days at temperatures of 20° C.

*Time to produce a rooted young plant, winter.*—About 24 to 26 days at temperatures of 20° C.

*Root description.*—Fibrous; color, close to 158A.

*Rooting habit.*—Freely branching; moderately dense to dense.

Plant description:

*Plant form/habit.*—Compact, outwardly spreading and mounded plant habit; outwardly spreading; vigorous growth habit. Freely branching habit with two lateral branches developing at every node.

*Plant height.*—About 14 cm.

*Plant width* (*spread*).—About 45 cm.

*Lateral branches.*—Length: About 6 cm to 9 cm. Diameter: About 1.2 mm. Internode length: About 1.6 cm to 2.6 cm. Strength: Strong; flexible. Texture: Pubescent. Color: 146C to 146D.

Foliage description:

*Arrangement.*—Opposite, simple; sessile.

*Length.*—About 1.6 cm to 2.9 cm.

*Width.*—About 9 mm to 12 mm.

*Shape.*—Lanceolate to elliptic.

*Apex.*—Acute.

*Based.*—Obtuse.

*Margin.*—Entire.

*Texture, upper surface.*—Pubescent.

*Texture, lower surface.*—Smooth, glabrous.

*Venation pattern.*—Pinnate.

*Color.*—Developing leaves, upper surface: 137A. Developing leaves, lower surface: 138B. Fully expanded leaves, upper surface: 147A; venation, 147C. Fully expanded leaves, lower surface: 147B; midvein, 147B; lateral veins, 147A.

Inflorescence description:

*Appearance.*—Daisy-type inflorescence form with elongated oblong-shaped ray florets. Inflorescences borne above and beyond the foliage. Disk and ray florets arranged acropetally on a capitulum. Inflorescences not fragrant.

*Flowering season.*—Plants flower from April until frost in Germany; flowering continuous during this period. Inflorescences not persistent. Freely flowering habit with about four to seven inflorescences per lateral branch

*Inflorescence bud.*—Height: About 2.9 mm. Diameter: About 4.25 mm. Shape: Oblate. Color: Towards the apex, 146A; mid-section, 146B; towards the base, 146C.

*Inflorescence size.*—Diameter: About 1.55 cm. Depth (height): About 4.5 mm. Diameter of disc: About 5.6 mm. Receptacle height: About 1.7 mm. Receptacle diameter: About 1 mm.

*Ray florets.*—Shape: Elongated-oblong. Orientation: Initially upright, then about 90° from vertical or perpendicular to peduncle. Length: About 6.3 mm. Width: About 2.4 mm. Apex: Emarginate to obtuse. Base: Fused into a short corolla tube. Margin: Entire. Texture, upper and lower surfaces: Smooth, glabrous, satiny. Number of ray florets per inflorescence: About 12 to 13 arranged in a single whorl. Color: When opening, upper surface: 13A. When opening, lower surface: 144A to 144B. Fully opened, upper surface: 14A. Fully opened, lower surface: N144A; color becoming closer to 144B with development; venation, 144A.

*Disc florets.*—Arrangement: Massed at center of receptacle. Shape: Tubular, elongated. Apex: Five-pointed. Length: About 2.1 mm. Width, at apex: About 1 mm. Width, at base: About 0.2 mm. Color: Immature: Apex: 151 A. Mid-section and base: 145C. Mature: Apex: 7A. Mid-section and base: 145C.

*Phyllaries.*—Number of phyllaries per inflorescence: About five fused at the base in a single whorl. Length: About 4.8 mm. Width: About 3.8 mm. Shape: Nearly round to obcordate. Apex: Acute. Margin: Entire. Texture, upper and lower surfaces: Smooth, glabrous. Color, upper and lower surfaces: 146A to 146B.

*Peduncles.*—Length: About 2.7 cm. Diameter: About 0.9 mm. Strength: Strong, flexible. Texture: Smooth, glabrous. Color: 146C to 146D.

*Reproductive organs.*—Androecium: Present on disc florets only. Filament length: About 2.2 mm. Filament color: 155D. Anther length: Less than 1 mm. Anther shape: Oblong. Anther color: 6A. Pollen amount: Scarce. Pollen color: 6A. Gynoecium: Present on both ray and disc florets. Pistil length: About 3 mm. Stigma shape: Two-parted. Stigma color: 17B. Style length: About 1.4 mm. Style color: 17D. Ovary color: 145A to 145C.

*Seeds.*—Quantity per flower: Typically 13. Length: About 1.5 mm to 2 mm. Diameter: About 0.8 mm. Color: 197A.

Disease/pest resistance: Plants of the new *Sanvitalia* have not been noted to be resistant to pathogens and pests common to *Sanvitalia.*

Garden performance: Plants of the new *Sanvitalia* have been observed to have good garden performance and tolerate rain, wind and temperatures from about 5° C. to about 30° C.

It is claimed:

1. A new and distinct *Sanvitalia* plant named 'Wessateq' as illustrated and described.

* * * * *

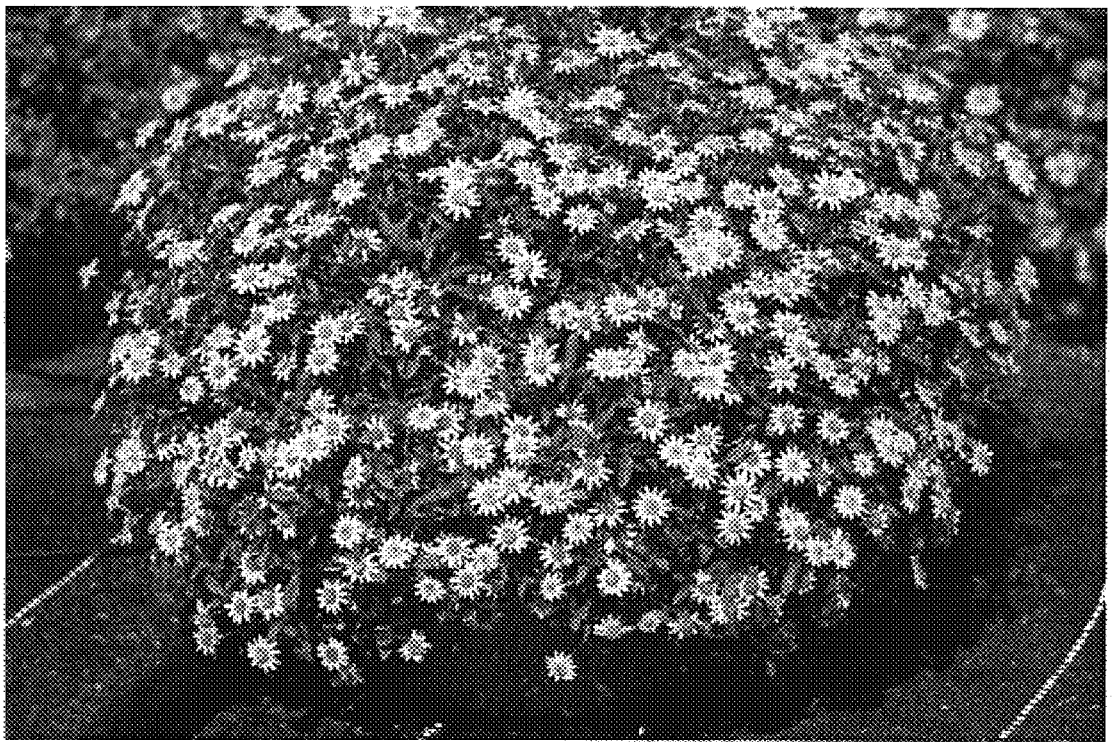

UNITED STATES PATENT AND TRADEMARK OFFICE

CERTIFICATE OF CORRECTION

PATENT NO. : PP 19,692 P2
APPLICATION NO. : 11/983741
DATED : February 10, 2009
INVENTOR(S) : Heinrich Westhoff It is certified that error appears in the above-identified patent and that said Letters Patent is hereby corrected as shown below:

Title Page, Item (50) Latin Name:
VARIETAL DENOMINATION should be “WESSATEQ”, not “WESSATEO”

Signed and Sealed this

Twenty-eighth Day of April, 2009

JOHN DOLL
*Acting Director of the United States Patent and Trademark Office*